United States Patent
Yoshikawa et al.

(10) Patent No.: US 10,093,550 B2
(45) Date of Patent: Oct. 9, 2018

(54) METHOD FOR MANUFACTURING HEXAGONAL PLATE-SHAPED ZINC OXIDE PARTICLES

(71) Applicants: NGK INSULATORS, LTD., Nagoya-shi (JP); NAGOYA INSTITUTE OF TECHNOLOGY, Nagoya-shi (JP)

(72) Inventors: Jun Yoshikawa, Nagoya (JP); Tsutomu Nanataki, Nagoya (JP); Tomokatsu Hayakawa, Nagoya (JP)

(73) Assignees: NGK Insulators, Ltd., Nagoya (JP); Nagoya Institute of Technology, Nagoya (JP)

(*) Notice: Subject to any disclaimer, the term of this patent is extended or adjusted under 35 U.S.C. 154(b) by 20 days.

(21) Appl. No.: 15/336,937

(22) Filed: Oct. 28, 2016

(65) Prior Publication Data
US 2017/0044022 A1  Feb. 16, 2017

Related U.S. Application Data

(63) Continuation of application No. PCT/JP2015/055927, filed on Feb. 27, 2015.

(51) Int. Cl.
*C01G 9/02* (2006.01)
*A61K 8/27* (2006.01)
(Continued)

(52) U.S. Cl.
CPC ............. *C01G 9/02* (2013.01); *A61K 8/0245* (2013.01); *A61K 8/0254* (2013.01); *A61K 8/27* (2013.01);
(Continued)

(58) Field of Classification Search
CPC ............ Y10T 428/2982; C01P 2006/12; C01P 2004/20; C01P 2004/03; C01P 2002/54; C01P 2002/52; C01P 2004/61; C01G 9/02
See application file for complete search history.

(56) References Cited

U.S. PATENT DOCUMENTS

| 2014/0050925 A1 | 2/2014 | Sueda et al. |
| 2015/0099122 A1 | 4/2015 | Yoshikawa et al. |

FOREIGN PATENT DOCUMENTS

| CN | 102659168 A | 9/2012 |
| JP | 2008-230877 A1 | 10/2008 |

(Continued)

OTHER PUBLICATIONS

CHi-Liang Kuo et al. "Hydrothermal Synthesis of ZnO Microspheres and Hexagonal Microrods with Sheetlike and Platelike Nanostructures" J. Phys. Chem. B 2005, 109, 20115-20121.*

(Continued)

*Primary Examiner* — Amber R Orlando
*Assistant Examiner* — Syed T Iqbal
(74) *Attorney, Agent, or Firm* — Burr & Brown, PLLC

(57) ABSTRACT

A method of producing hexagonal plate-like zinc oxide particles having a sharp particle size distribution (i.e., a relatively uniform particle size) at a high weight yield and a high percent yield is provided. The method of producing hexagonal plate-like zinc oxide particles of the present invention comprises mixing by stirring an aqueous hexamethylenetetramine (HMT) solution, a solution of an anionic surfactant in a water-insoluble organic solvent, and optionally water to form a microemulsion containing an aqueous phase of an aqueous hexamethylenetetramine solution having a molar concentration of 0.05 M or more; dropwise adding an aqueous zinc salt solution to the microemulsion; and heating the microemulsion containing the aqueous zinc salt solution to a reaction temperature of 80° C. or more (Continued)

without using any autoclave to form hexagonal plate-like zinc oxide particles.

13 Claims, 1 Drawing Sheet

(51) Int. Cl.
*A61Q 1/00* (2006.01)
*A61Q 19/00* (2006.01)
*A61K 8/02* (2006.01)

(52) U.S. Cl.
CPC .......... *A61Q 19/00* (2013.01); *A61K 2800/10* (2013.01); *C01P 2002/50* (2013.01); *C01P 2002/52* (2013.01); *C01P 2004/03* (2013.01); *C01P 2004/22* (2013.01); *C01P 2004/51* (2013.01); *C01P 2004/53* (2013.01); *C01P 2004/61* (2013.01); *C01P 2004/62* (2013.01)

(56) References Cited

FOREIGN PATENT DOCUMENTS

| JP | 2013-245139 A1 | 12/2013 |
|---|---|---|
| WO | 2012/147886 A1 | 11/2012 |
| WO | 2014/007045 A1 | 1/2014 |

OTHER PUBLICATIONS

Li et al. "Growth of well-defined ZnO microparticles with additives from aqueous solution" Journal of Solid State Chemistry 178 (2005) 855-860.*

Gui Han, et al., "Nanosized Hexagonal Platelike ZnO for Nanophosphor Applications," *J Vac. Sci. Technol.*, B28(2), Mar./Apr. 2010, pp. C2C16-C2C19.

Gui Han, et al., "Cathodoluminescence of Single Disk-Like ZnO Prepared by Low Temperature Solution-Based Method," *e-Journal of Surface Science and Nanotechnology*, vol. 7 (2009), pp. 354-357.

International Search Report and Written Opinion (Application No. PCT/JP2015/055927) dated May 26, 2015 (with English translation).

* cited by examiner

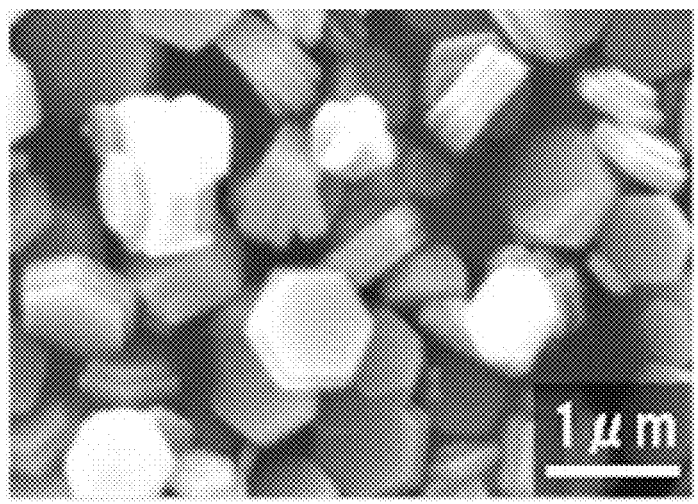

METHOD FOR MANUFACTURING HEXAGONAL PLATE-SHAPED ZINC OXIDE PARTICLES

CROSS-REFERENCE TO RELATED APPLICATIONS

This application is a continuation application of PCT/JP2015/055927 filed Feb. 27, 2015, which claims priority to Japanese Patent Application No. 2014-094856 filed May 1, 2014, the entire contents all of which are incorporated herein by reference.

BACKGROUND OF THE INVENTION

1. Field of the Invention

The present invention relates to a method of producing hexagonal plate-like zinc oxide particles.

2. Description of the Related Art

Hexagonal plate-like zinc oxide particles are used in powder forms for a variety of purposes, such as cosmetics and paints. The particles formed into oriented sintered compacts also can be used in other purposes, such as thermoelectric materials and sputtering targets.

For example, Patent Document 1 (WO2012/147886) discloses hexagonal plate-like zinc oxide particles having a primary particle diameter of 0.01 μm or more and an aspect ratio of 2.5 or more and discloses that the hexagonal plate-like zinc oxide particles can be used as components of cosmetics, heat-dissipating fillers, heat-dissipating resin compositions, heat-dissipating grease, and heat-dissipating paint compositions. In this document, the hexagonal plate-like zinc oxide particles are produced by ripening zinc oxide microparticles in an aqueous zinc salt solution, where the zinc oxide microparticles preferably have a particle diameter of 0.005 μm or more and 0.05 μm or less. It is believed that the zinc oxide microparticles function as seed crystals.

Methods of producing hexagonal plate-like zinc oxide particles without using any seed crystal are also known. For example, Nonpatent Document 1 (G. Han et al., J. Vac. Sci. Technol. B28(2), C2C16-C2C19 (2010)) discloses a method of producing hexagonal plate-like zinc oxide particles, wherein deionized water and an aqueous 0.10 M hexamethylenetetramine (hereinafter, HMT) solution are added to a solution of 0.10 M sodium di(2-ethylhexyl)sulfosuccinate (hereinafter, AOT) in 1-butanol to produce a microemulsion; an aqueous 0.10 M $Zn(NO_3)_2$ solution is added to the microemulsion, followed by mixing by stirring; the resulting mixed solution is gradually warmed to 75° C. and is maintained at this temperature for 3 to 4 hours; and the precipitate is collected by filtration and dried to give hexagonal plate-like zinc oxide particles. Nonpatent Document 2 (G. Han et al., e-J. Surf. Sci. Nanotech. Vol. 7 (2009) 354-357) discloses a method of producing hexagonal plate-like zinc oxide particles, wherein an aqueous solution of a mixture of 0.10 M HMT and 0.10 M $Zn(NO_3)_2$ is added to a solution of 0.10 M AOT in 1-butanol, followed by stirring; the mixture is maintained at 90° C. for 12 hours in an autoclave; and the resulting white suspension is centrifuged, washed, and dried to give hexagonal plate-like zinc oxide particles.

CITATION LIST

Patent Document

Patent Document 1: WO2012/147886

Nonpatent Documents

Nonpatent Document 1: G. Han et al., J. Vac. Sci. Technol. B28(2), C2C16-C2C19 (2010)
Nonpatent Document 2: G. Han et al., e-J. Surf. Sci. Nanotech. Vol. 7 (2009) 354-357

SUMMARY OF THE INVENTION

Since the method described in Patent Document 1 uses zinc oxide microparticles as seed crystals, a single particle may have heterogeneous crystallinity and impurity distribution (because the particle contains a crystalline portion derived from the seed crystal), for example. In contrast, the methods not using any seed crystal described in Nonpatent Documents 1 and 2 have problems in that the percent yield of the hexagonal plate-like particles against the raw materials and the weight yield per unit reaction solution are significantly low and that the particle size distribution becomes broad with an increase in the particle size. In particular, since a broad particle size distribution of hexagonal plate-like particles causes disadvantages, such as a decrease in coating characteristics when used in a powder form and a decrease in sintering characteristics when used in sintering, it is desirable that hexagonal plate-like zinc oxide particles have a small particle size distribution (i.e., a relatively uniform particle size).

The present inventors have found that hexagonal plate-like zinc oxide particles having a sharp particle size distribution (i.e., a relatively uniform particle size) can be produced at a high weight yield and a high percent yield by dropwise adding an aqueous zinc salt solution to a microemulsion containing an aqueous phase of an aqueous hexamethylenetetramine solution having a molar concentration of 0.05 M or more and heating the mixture to a reaction temperature of 80° C. or more without using any autoclave.

A purpose of the present invention is accordingly to produce hexagonal plate-like zinc oxide particles having a sharp particle size distribution (i.e., relatively uniform particle size) at a high weight yield and a high percent yield.

An embodiment of the present invention provides a method of producing hexagonal plate-like zinc oxide particles, comprising:
  mixing by stirring an aqueous hexamethylenetetramine (HMT) solution, a solution of an anionic surfactant in a water-insoluble organic solvent, and optionally water to form a microemulsion containing an aqueous phase of an aqueous hexamethylenetetramine solution having a molar concentration of 0.05 M or more;
  dropwise adding an aqueous zinc salt solution to the microemulsion; and
  heating the microemulsion containing the aqueous zinc salt solution to a reaction temperature of 80° C. or more without using any autoclave to form hexagonal plate-like zinc oxide particles.

BRIEF DESCRIPTION OF DRAWING

FIG. 1 is an SEM photograph of a hexagonal plate-like zinc oxide powder prepared in Example 6.

DETAILED DESCRIPTION OF THE INVENTION

Method of Producing Hexagonal Plate-Like Zinc Oxide Particles

The present invention relates to a method of producing hexagonal plate-like zinc oxide particles. The hexagonal plate-like zinc oxide particles are zinc oxide crystal particles having a hexagonal crystal wurtzite structure and are basically single crystal particles. In the method of the present invention, an aqueous hexamethylenetetramine (HMT) solution (hereinafter, referred to as aqueous HMT solution), a solution of an anionic surfactant in a water-insoluble organic solvent, and optionally water are mixed by stirring to form a microemulsion containing an aqueous phase of an aqueous HMT solution having a molar concentration of 0.05 M or more. An aqueous zinc salt solution is then dropwise added to the microemulsion. Subsequently, the microemulsion containing the aqueous zinc salt solution is heated to a reaction temperature of 80° C. or more without using any autoclave to form hexagonal plate-like zinc oxide particles.

In this procedure, hexagonal plate-like zinc oxide particles having an unexpectedly sharp particle size distribution can be produced at surprisingly high weight yield and percent yield by, in particular, increasing the HMT concentration in the microemulsion to 0.05 M or more and raising the reaction temperature to 80° C. or more. A sharp particle size distribution indicates that the particle size is relatively uniform. The hexagonal plate-like zinc oxide particles having a relatively uniform particle size have extremely great deal of potential in various fields using zinc oxide particles. The use of such zinc oxide particles in film formation, molding, and/or sintering can prepare a zinc oxide film, a zinc oxide molded product, and/or a zinc oxide sintered compact with higher homogeneity and higher quality. A relatively uniform particle size has advantages, such as improvements in coating characteristics when used in a powder form and improvements in sintering characteristics when used in sintering. In addition, since the method of the present invention does not use any seed crystal, for example, crystallinity and impurity distribution in a single particle hardly become heterogeneous (because the particle does not contain a crystalline portion derived from a seed crystal) to provide hexagonal plate-like zinc oxide particles having excellent homogeneity. Furthermore, the method of the present invention does not need to use an autoclave, which is a large-scale apparatus (because accompanying high-temperature and high-pressure reaction conditions), and therefore has an advantage of being carried out with a relatively simple system configuration.

(1) Generation of Microemulsion

An aqueous HMT solution, a solution of an anionic surfactant in a water-insoluble organic solvent, and optionally water are mixed by stirring to form a microemulsion containing an aqueous phase of an aqueous HMT solution having a molar concentration of 0.05 M or more. The microemulsion is one type of emulsion. The microemulsion is composed of liquid components that are not mutually dissolved in such a manner that nanodroplets (having a diameter of several nanometers to a hundred nanometer, for example) of one of the liquid components are dispersed in the other liquid component, and has a transparent or translucent (typically, colorless transparent) appearance.

The aqueous HMT solution may have any initial concentration that allows the resulting microemulsion to have a predetermined concentration of the HMT in the aqueous phase of the microemulsion. Accordingly, in the production of the microemulsion, water may be further added to the microemulsion as needed. The molar concentration of the aqueous HMT solution in the microemulsion is preferably 0.05 M or more, more preferably 0.10 M or more, more preferably 0.25 M or more, and most preferably 0.50 M or more. An increase in the molar concentration of the aqueous HMT solution contributes to an improvement in the percent yield of hexagonal plate-like zinc oxide particles. Although the molar concentration of the aqueous HMT solution in the microemulsion does not have an upper limit, the concentration is typically 2.0 M or less, exemplarily 1.0 M or less.

It is noted that the molar concentration of the aqueous HMT solution in the microemulsion is desirably determined in consideration of the balance with the molar concentration of the aqueous zinc salt solution. Specifically, the molar concentration ratio of the aqueous HMT solution to the aqueous zinc salt solution in the microemulsion is preferably within a range of 0.5 to 1.0, more preferably 0.5 to 0.8, and most preferably 0.6 to 0.8. A molar concentration ratio within this range contributes to an increase in percent yield.

The solution of an anionic surfactant in a water-insoluble organic solvent is prepared separately from the aqueous HMT solution and is mixed with the aqueous HMT solution and optionally water during the production of the microemulsion. Any water-insoluble organic solvent that can achieve desired particle size distribution, weight yield, and percent yield can be used. Preferred examples of the water-insoluble organic solvent include alcohols having 4 to 8 carbon atoms, ethers having 4 to 10 carbon atoms, and ketones having 4 to 10 carbon atoms, such as 1-butanol, diethyl ether, and methyl isobutyl ketone. The most preferred water-insoluble organic solvent is 1-butanol. Any anionic surfactant that can achieve desired particle size distribution, weight yield, and percent yield can be used. Examples of the anionic surfactant include sulfonate surfactants, such as sodium di(2-ethylhexyl)sulfosuccinate (hereinafter, referred to as AOT); sulfate surfactants, such as sodium dodecylsulfate (SDS); carboxylate surfactants, such as sodium fatty acid; and phosphate surfactants, such as sodium monoalkylphosphate. The most preferred anionic surfactant is AOT. In the case of using AOT, the concentration of the AOT solution (e.g., AOT/1-butanol solution) is preferably 0.01 to 1 M and more preferably 0.05 to 0.5 M.

(2) Dropwise Addition of Aqueous Zinc Salt Solution

An aqueous zinc salt solution is then dropwise added to the resulting microemulsion. This dropwise addition of the aqueous zinc salt solution is carried out preferably over one minute or more, more preferably 2 minutes or more, more preferably 3 minutes or more, and most preferably 3 to 10 minutes. A dropping time within such a range can provide a sharp particle size distribution. Preferred examples of the zinc salt include zinc sulfate, zinc nitrate, zinc chloride, organic acid salts (e.g., zinc acetate), and zinc alkoxides. The most preferred zinc salt is zinc nitrate. The concentration of the aqueous zinc salt solution is preferably 0.01 M or more, more preferably 0.05 M or more, more preferably 0.2 M or more, and most preferably 0.8 M or more. Although the concentration of the aqueous zinc salt solution does not have an upper limit, the concentration is typically 3.0 M or less, exemplarily 2.0 M or less.

A particularly preferred microemulsion contains the aqueous HMT solution at a molar concentration of 0.5 M or more and the aqueous zinc salt solution at a concentration of 0.8 M or more. Such a microemulsion enables production of hexagonal plate-like zinc oxide particles having an extremely sharp particle size distribution with remarkably high weight yield and percent yield. The use of the aqueous HMT solution and the aqueous zinc salt solution having such high concentrations can achieve a high weight yield with a relatively small reaction apparatus.

(3) Heating of Microemulsion

Subsequently, the resulting microemulsion containing the aqueous zinc salt solution is heated to a reaction temperature of 80° C. or more without using any autoclave to form hexagonal plate-like zinc oxide particles. A reaction temperature of 80° C. or more enables generation of hexagonal plate-like zinc oxide particles having a sharp particle size distribution. The reaction temperature is 80° C. or more, preferably 85° C. or more, and more preferably 85° C. to 95° C. Preferably, this reaction temperature is gradually raised at a rate of 5° C./min or less, more preferably 3° C./min or less, and more preferably 1° C./min to 3° C./min. A heating rate controlled within such a range can provide a further sharp particle size distribution. The microemulsion is preferably maintained at the reaction temperature for 1 hour or more, more preferably 1 to 5 hours, and most preferably 2 to 4 hours.

(4) Optional Step

The resulting hexagonal plate-like zinc oxide particles are preferably subjected to separation, drying, and/or heat treatment. The separation is preferably performed by, for example, centrifugation, preferably while washing with a solvent, such as ion exchanged water or ethanol. The drying may be performed under any conditions. Although the drying may be performed at ordinary temperature, heating to a predetermined temperature (for example, 60° C. to 150° C.) is preferred from the viewpoint of production efficiency. The heat treatment may also be performed under any conditions, but is preferably performed in an appropriate atmosphere (e.g., air atmosphere), for example, at 500° C. to 1000° C. for 0.5 to 3 hours, for sufficiently removing the organic components that may remain in the solid matter represented by the hexagonal plate-like zinc oxide particles.

Hexagonal Plate-Like Zinc Oxide Particle

The hexagonal plate-like zinc oxide particles prepared by the method of the present invention have a sharp particle size distribution (i.e., a relatively uniform particle size). In addition, the method of the present invention can produce such hexagonal plate-like zinc oxide particles with a high weight yield and a high percent yield. This sharp particle size distribution can be evaluated by the ratio of the particle diameter D90 to the particle diameter D10 (i.e., ratio D90/D10). A smaller D90/D10 ratio indicates a sharper particle size distribution. Specifically, the hexagonal plate-like zinc oxide particles preferably have a D90/D10 ratio of 4.00 or less, more preferably 3.50 or less, more preferably 3.30 or less, and most preferably 3.00 or less. Since a lower D90/D10 ratio is desirable, the D90/D10 ratio should not have a lower limit, but is within a range of 2.00 or more, 2.30 or more, or 2.50 or more in practice. The hexagonal plate-like zinc oxide particles preferably have a volume average particle diameter D50 of 0.70 to 2.00 µm from the viewpoint of readily producing a dense sintered compact. The particle diameter D10, particle diameter D90, and average particle diameter D50 described in the present specification are all on the basis of volume and can be measured with a commercially available laser diffraction particle-size-distribution analyzer.

Since the hexagonal plate-like zinc oxide particles have a shape like a plate, the particles can be produced into a molded product or sintered compact containing oriented plate-like particles by a molding process involving applying a shearing force to the plate-like particles, such as tape casting and extrusion molding. The shearing force can control the orientation of the plate-like particles.

The hexagonal plate-like zinc oxide particles may further contain any additive. The additive may be added to a stock solution for the hexagonal plate-like zinc oxide particles and thereby may be preliminary dissolved in the form of solid solution in the particles. Alternatively, the additive may be mixed with the hexagonal plate-like zinc oxide particles and then be dissolved in the form of solid solution in the particles during the formation of a sintered compact. The additive can be an additive or dopant that can impart desired characteristics (e.g., electroconductivity or insulation) to the molded product, according to the use or specification of the product. Preferred examples of the dopant element include B, Al, Ga, In, C, F, Cl, Br, I, H, Li, Na, K, N, P, As, Cu, Ag, and combinations thereof. Preferred examples of n-type dopant element include B, Al, Ga, In, C, F, Cl, Br, I, and combinations thereof. Preferred examples of p-type dopant element include H, Li, Na, K, N, P, As, C, Cu, Ag, and combinations thereof.

EXAMPLES

The present invention will be described in further detail by the following examples.

Example 1 (Comparison)

Sodium di(2-ethylhexyl)sulfosuccinate (AOT, manufactured by Alfa Aesar) and 1-butanol were mixed to prepare a 0.1 M AOT/1-butanol solution. Separately, hexamethylenetetramine (HMT, manufactured by Sigma-Aldrich Corporation) and ultrapure water (Milli-Q water) were mixed to prepare an aqueous 0.1 M HMT solution. The 0.1 M AOT/1-butanol solution (10 mL), the aqueous 0.1 M HMT solution (25 mL), and Milli-Q water (50 mL) were vigorously stirred. Since water is immiscible with 1-butanol, the mixture was cloudy at the beginning of the stirring, but became colorless transparent by continuing the vigorous stirring to give a microemulsion. On this occasion, the HMT concentration in the microemulsion was calculated to be 0.033 M supposing that the HMT was present in the aqueous phase. Aside from this, $Zn(NO_3)_2 \cdot 6H_2O$ (manufactured by Kishida Chemical Co., Ltd.) and Milli-Q water were mixed to prepare an aqueous 0.1 M $Zn(NO_3)_2$ solution. The aqueous 0.1 M $Zn(NO_3)_2$ solution (25 mL) was then dropwise added over 5 minutes with a dropper to the microemulsion while being agitated with a stirrer. The temperature of the solution was raised at a rate of 1.6° C./min from 25° C. to 70° C. over 28 minutes while the solution was being agitated with a hot stirrer. The solution was maintained at 70° C. for 3 hours and was then taken off the hot stirrer, for natural cooling. After the supernatant was removed, the resulting solid matter was subjected to a washing operation. The washing operation was carried out with a centrifuge using ethanol and then ion exchanged water as solvents, and this operation was repeated. The resulting solid matter was dried at 80° C. with a drier. In order to remove the organic components slightly remaining in the solid matter, heat treatment at 900° C. was carried out in the air for 1 hour to give hexagonal plate-like zinc oxide powder.

The crystal phase of the resulting powder observed with an X-ray diffractometer (XRD) was a single ZnO phase. The weight of the powder was 0.096 g, which corresponds to a percent yield of 47.3% where the percent yield is 100% when all the raw material is changed to ZnO. The total volume of the solution in this example was 110 mL. The weight yield for 1 L of the solution therefore corresponds to 0.87 g. The particle size distribution was measured with a laser diffraction particle-size-distribution analyzer (Product model No.: MT3300EXII, manufactured by Nikkiso Co., Ltd.), and the average particle diameter D50 was 0.38 µm. The value D90/D10 indicating the sharpness of a particle size distribution was 4.85.

Example 2 (Comparison)

A hexagonal plate-like zinc oxide powder was produced and evaluated as in Example 1 except that the reaction temperature was 75° C.

Example 3 (Comparison)

A hexagonal plate-like zinc oxide powder was produced and evaluated as in Example 1 except that the reaction temperature was 80° C.

Example 4 (Comparison)

A hexagonal plate-like zinc oxide powder was produced and evaluated as in Example 1 except that the reaction temperature was 85° C.

Example 5 (Comparison)

A hexagonal plate-like zinc oxide powder was produced and evaluated as in Example 1 except that the reaction temperature was 90° C.

Example 6

A hexagonal plate-like zinc oxide powder was produced and evaluated as in Example 1 except that the HMT concentration in the microemulsion was 0.067 M and the centration in the microemulsion was 0.67 M and the concentration of the dropwise added aqueous $Zn(NO_3)_2$ solution was 1 M.

Example 9

A hexagonal plate-like zinc oxide powder was produced and evaluated as in Example 7 except that the zinc salt was $ZnCl_2$.

Example 10

A hexagonal plate-like zinc oxide powder was produced and evaluated as in Example 7 except that the aqueous zinc salt solution was dropwise added over one minute.

Example 11

A hexagonal plate-like zinc oxide powder was produced and evaluated as in Example 7 except that the temperature was raised at a rate of 6.4° C./min.

Example 12

A hexagonal plate-like zinc oxide powder was produced and evaluated as in Example 7 except that the HMT concentration in the microemulsion was 0.134 M.

Results

Table 1 shows the experimental conditions employed in Examples 1 to 12 and the results of the evaluation. The results of XRD analysis demonstrated that the powders prepared in Examples 2 to 12 were of single ZnO phases as in Example 1.

TABLE 1

| | Experimental conditions | | | | | Characteristics | | | |
|---|---|---|---|---|---|---|---|---|---|
| | Concentration | | | Time for dropping | | | | | |
| | Reaction temperature [° C.] | Concentration of aqueous HMT solution in microemulsion [M] | Concentration of aqueous zinc salt solution [M] | Ratio of (aqueous HMT solution conc. [M])/ (aqueous zinc salt solution conc. [M]) | desired amount of aqueous zinc salt solution [min] | Temperature raising rate [° C./min] | Percent yield [%] | Weight yield for 1 L of solution [g] | Average particle size [μm] | Particle size distribution D90/D10 |
| Ex 1* | 70 | 0.033 | 0.1 | 0.33 | 5 | 1.6 | 47.3 | 0.87 | 0.38 | 4.85 |
| Ex 2* | 75 | 0.033 | 0.1 | 0.33 | 5 | 1.6 | 37.9 | 0.70 | 0.42 | 4.61 |
| Ex 3* | 80 | 0.033 | 0.1 | 0.33 | 5 | 1.6 | 55.7 | 1.03 | 0.78 | 4.92 |
| Ex 4* | 85 | 0.033 | 0.1 | 0.33 | 5 | 1.6 | 54.2 | 1.00 | 0.80 | 3.78 |
| Ex 5* | 90 | 0.033 | 0.1 | 0.33 | 5 | 1.6 | 54.7 | 1.01 | 0.89 | 3.55 |
| Ex 6 | 80 | 0.067 | 0.1 | 0.67 | 5 | 1.6 | 71.4 | 1.32 | 0.78 | 2.82 |
| Ex 7 | 90 | 0.067 | 0.1 | 0.67 | 5 | 1.6 | 70.0 | 1.29 | 0.93 | 2.91 |
| Ex 8 | 90 | 0.67 | 1.0 | 0.67 | 5 | 1.6 | 88.2 | 16.3 | 1.05 | 2.69 |
| Ex 9 | 90 | 0.067 | 0.1 | 0.67 | 5 | 1.6 | 70.5 | 1.30 | 0.88 | 2.90 |
| Ex 10 | 90 | 0.067 | 0.1 | 0.67 | 1 | 1.6 | 70.8 | 1.31 | 0.90 | 3.54 |
| Ex 11 | 90 | 0.067 | 0.1 | 0.67 | 5 | 6.4 | 71.5 | 1.32 | 0.81 | 3.81 |
| Ex 12 | 90 | 0.134 | 0.1 | 1.34 | 5 | 1.6 | 64.0 | 1.18 | 0.79 | 2.83 |

*Comparative Example reaction temperature was 80° C. FIG. 1 is an SEM photograph of the resulting hexagonal plate-like zinc oxide powder.

Example 7

A hexagonal plate-like zinc oxide powder was produced and evaluated as in Example 6 except that the reaction temperature was 90° C.

Example 8

A hexagonal plate-like zinc oxide powder was produced and evaluated as in Example 7 except that the HMT con-

What is claimed is:

1. A method of producing hexagonal plate-like zinc oxide particles, comprising:
    mixing by stirring an aqueous hexamethylenetetramine (HMT) solution; and a solution of an anionic surfactant in a water-insoluble organic solvent to form a microemulsion containing an aqueous phase of an aqueous hexamethylenetetramine solution having a molar concentration of 0.05 M or more;
    dropwise adding an aqueous zinc salt solution to the microemulsion; and heating the microemulsion containing the aqueous zinc salt solution to a reaction temperature of 80° C. or more without using any autoclave to form hexagonal plate-like zinc oxide particles.

2. The method according to claim 1, wherein the molar concentration ratio of the aqueous hexamethylenetetramine solution to the aqueous zinc salt solution in the microemulsion is within a range of 0.5 to 1.0.

3. The method according to claim 1, wherein the reaction temperature is raised at a rate of 5° C./min or less.

4. The method according to claim 1, wherein the aqueous zinc salt solution is dropwise added over 2 minutes or more.

5. The method according to claim 1, wherein the microemulsion is maintained at the reaction temperature for 1 hour or more.

6. The method according to claim 1, wherein the microemulsion contains the aqueous hexamethylenetetramine solution at a molar concentration of 0.5 M or more and the aqueous zinc salt solution at a concentration of 0.8 M or more.

7. The method according to claim 1, wherein the zinc salt is zinc nitrate.

8. The method according to claim 1, wherein the anionic surfactant is sodium di(2-ethylhexyl)sulfosuccinate (AOT).

9. The method according to claim 1, wherein the water-insoluble organic solvent is 1-butanol.

10. The method according to claim 1, further comprising:
separating, drying, and/or heat treating the hexagonal plate-like zinc oxide particles.

11. The method according to claim 1, wherein the hexagonal plate-like zinc oxide particles have a volume average particle diameter D50 of 0.70 to 2.00 µm.

12. The method according to claim 1, wherein the hexagonal plate-like zinc oxide particles have a particle size distribution represented by a ratio D90/D10 of 4.00 or less.

13. The method according to claim 1, wherein the mixing further includes water to form the microemulsion.

* * * * *

UNITED STATES PATENT AND TRADEMARK OFFICE
CERTIFICATE OF CORRECTION

| | |
|---|---|
| PATENT NO. | : 10,093,550 B2 |
| APPLICATION NO. | : 15/336937 |
| DATED | : October 9, 2018 |
| INVENTOR(S) | : Jun Yoshikawa, Tsutomu Nanataki and Tomokatsu Hayakawa |

It is certified that error appears in the above-identified patent and that said Letters Patent is hereby corrected as shown below:

On the Title Page

<u>Foreign Application Priority Data, Item (30)</u>
Please add:
"Foreign Application Priority Data May 1, 2014 (JP).....2014-094856"

Signed and Sealed this
Twenty-seventh Day of November, 2018

Andrei Iancu
*Director of the United States Patent and Trademark Office*